United States Patent [19]

Kesling

[11] Patent Number: 4,842,512

[45] Date of Patent: Jun. 27, 1989

[54] COMBINATION EDGEWISE BRACKET

[75] Inventor: Christopher K. Kesling, LaPorte, Ind.

[73] Assignee: TP Orthodontics, Inc., Westville, Ind.

[21] Appl. No.: 933,578

[22] Filed: Nov. 21, 1986

[51] Int. Cl.[4] ................................................ A61C 3/00
[52] U.S. Cl. ........................................ 433/8; 433/16
[58] Field of Search .................... 433/8, 9, 10, 11, 15, 433/16

[56] References Cited

U.S. PATENT DOCUMENTS

| | | | |
|---|---|---|---|
| 1,976,141 | 10/1934 | Richardson | 433/8 |
| 3,775,850 | 12/1973 | Northcutt | 433/9 |
| 3,838,514 | 10/1974 | Polak | 433/8 |
| 3,930,311 | 1/1976 | Andrews | 433/8 |
| 3,964,165 | 6/1976 | Stahl | 433/8 |
| 4,219,617 | 8/1980 | Wallshein | 433/8 |
| 4,242,085 | 12/1980 | Wallshein | 433/16 |
| 4,443,190 | 4/1984 | Kurz | 433/15 |
| 4,531,911 | 7/1985 | Creekmore | 433/8 |
| 4,669,980 | 6/1987 | Degnan | 433/9 |

OTHER PUBLICATIONS

"Principles and Technique of Modified Edgewise Arch Mechanism", Alexander Sved, American Journal of Orthodontics and Oral Surgery, vol. 24, No. 7, Jul., 1938, pp. 635–654.
Unitek Catalog 116, copyright 1973, pp. 37 and 41.

Primary Examiner—John J. Wilson
Attorney, Agent, or Firm—Lloyd L. Zickert

[57] ABSTRACT

A combination edgewise bracket for selective use in crown tipping root uprighting or torquing, which includes a pair of labiobuccally opening archwire slots one of which when coacting with an archwire and there being selective forces applied between the archwire and bracket will allow crown tipping and root uprighting movements and the other of which when coacting with a rectangular archwire may provide both torquing and mesio-distal axial control. The other slot may function to cause or stabilize tooth movement in three dimensions.

17 Claims, 1 Drawing Sheet

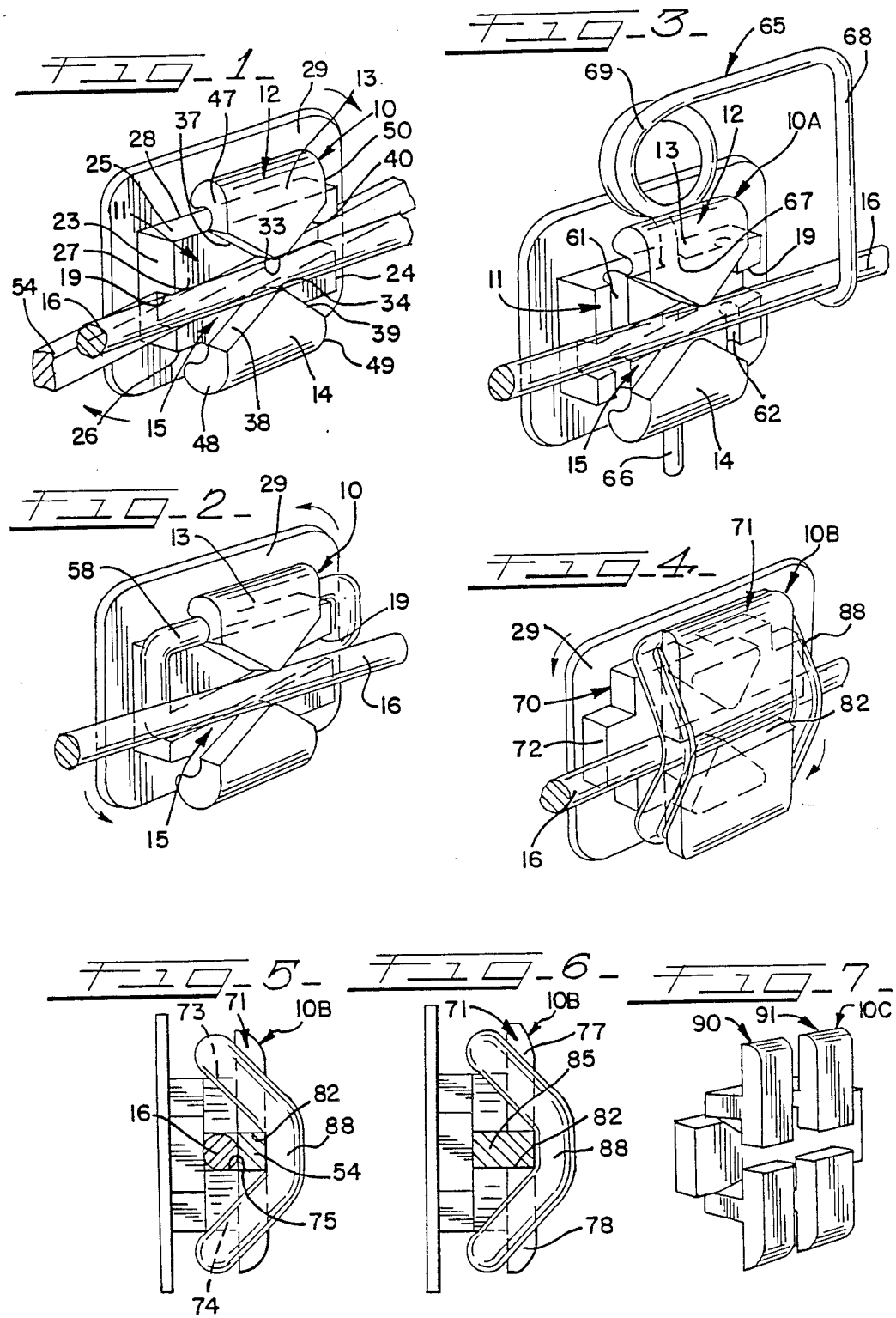

COMBINATION EDGEWISE BRACKET

DESCRIPTION

This invention relates in general to an orthodontic bracket for use with one or more archwires and force-producing devices to produce selected tooth movement, and more particularly, to an orthodontic bracket capable of permitting mesial-distal tooth movement through crown tipping and uprighting movements, and torquing movements, and still more particularly to an edgewise bracket capable of moving teeth with intraoral generated forces while permitting a range of free crown tipping and producing predetermined final degree values of root uprighting movement and/or selected torque movement.

The terms "tipping", "uprighting" and "torquing" relate to movements of teeth caused by the application of selected forces. Generally, "tipping" refers to either labial-lingual or mesial-distal movement of the crown of a tooth, while "uprighting" refers to either mesial or distal movement of the tip (apex) of the root of a tooth. Tipping herein will be in the mesial-distal direction unless otherwise specified. "Torquing" generally refers to the movement of the root of a tooth in the labial-lingual direction as a result of forces being applied to the crown of the tooth. Thus, crown movement will be referred to as tipping, while root movement will be referred to as uprighting or torquing. The use of "and-/or" herein is intended to cover three alternatives. For example, "force and/or time" means force and time or force or time.

BACKGROUND OF THE INVENTION

There area a number of orthodontic techniques in use, the most common being the edgewise and the Begg techniques. Within the ambit of the edgewise technique, the most popular form is referred to as the straight-wire technique, although all forms of edgewise technique generally use edgewise brackets having horizontally extending rectangular archwire slots, the openings of which face horizontally. The bracket configuration for the Begg technique utilizes a vertically extending archwire slot which permits materially greater free tipping of teeth during treatment than heretofore known edgewise brackets. Free tipping action with edgewise brackets is very limited and only possible when a wire smaller than the archwire slot is employed, so that there is a sloppy or loose fit between the archwire and the slot.

The need for moving teeth mesiodistally is usually caused by spaces created by small or missing teeth. It is customary in the Begg technique to close these spaces or move teeth by first tipping the crowns toward the open area and then uprighting the root so that the final uprighting or tip angle of the crown is at a predetermined inclination. For closing such open sites when using the edgewise technique, it is customary to bodily move the teeth. It is well known that the forces needed, discomfort, and time required for closing spaces by tipping and uprighting movements are much less than that required for bodily moving the teeth.

Where teeth are initially tipped and standard edgewise brackets are mounted on the teeth to provide treatment through the edgewise technique, it is difficult, if not impossible, to engage a relatively large diameter or stiff archwire into the respective archwire slots. The same problem exists if teeth with edgewise brackets become tipped during the course of treatment. And yet, such larger diameter, stiffer archwires are often necessary to control the vertical and horizontal positions of the teeth in the jaws. Therefore, weaker and more flexible archwires must be utilized which can cause the anterior teeth to elongate. The most common method of preventing elongation includes application of heavy extraoral forces to the upper archwire.

If resilient archwires are deflected to fully engage angulated slots where teeth are tipped, the occlusal plane or level of the biting edges of the teeth can be adversely affected by the forces applied through these archwires. Usually, the anterior teeth are elevated out of their sockets, resulting in an unhealthy deep anterior overbite condition. This is one of the reasons tipping of teeth in the edgewise technique is avoided. Moreover, the very design of the well known edgewise bracket prevents teeth from becoming tipped during treatment. It will be understood that the "occlusal plane" as used herein is a plane containing the contact points between the upper and lower teeth, and it generally lies ninety degrees to the vertical lines used for references when determining and describing the amount of tip desired for each tooth.

In Begg brackets, sometimes referred to as ribbon arch or lightwire brackets, it is usually possible to engage larger stiffer archwires in the archwire slots because the opening of the slots face vertically, thereby permitting ease of archwire engagement in brackets mounted on tipped teeth.

It has been suggested that the edgewise slot be shortened mesiodistally or altered to define opposing one point contacts to increase the degree of tipping. However, the former still restricts tipping and loses its effectiveness to control/achieve the final degree of uprighting desired. The latter (altered) bracket can permit free tipping but has no ability to control or create the final, desired degree of uprighting.

While Begg brackets that permit but limit tipping and/or uprighting are known, edgewise brackets with similar functions are not known, except a bracket long ago developed by Alexander Sved. The Sved bracket allowed unlimited tipping and uprighting movements and included a horizontal archwire slot, hereinafter called "Sved shaped", that included pivot edges and surfaces widely diverging from the pivot edges. The Sved bracket is shown in the July, 1938 issue of the American Journal of Orthodontics, pages 635–654.

It has also been known to use combination brackets having both labially or horizontally facing horizontal archwire slots and gingivally facing vertical archwire slots where the vertical slots would be used during early stages of orthodontic treatment to allow the crowns of the teeth to tip toward their final positions. Then in the final stage an archwire can be deflectively received by the horizontal slots. However, while this will tend to upright the teeth, it will also tend to deepen the anterior bite condition and therefore headgear for producing extraoral forces may be required to counteract such adverse conditions. Headgear comprises using the patient's head or neck as a point of anchorage for delivering relatively heavy forces to the teeth.

Where combination brackets are used, it has also been suggested that two archwires be used, one in the horizontal slots and one in the vertical slots. A lighter more resilient archwire is deflected to seat in the angulated horizontal slots, while a heavier stiffer archwire is engaged without deflection into the vertical slots. The heavy wire helps stabilize the reciprocal forces delivered to the teeth from the lighter deflected archwire as it returns to its passive straight arch form.

In the edgewise procedure teeth are moved bodily in their upright positions toward one another to close spaces. Such movement requires up to twice as much force and/or time as when moving teeth in the Begg technique by a combination of tipping and uprighting forces. Normally, the crown tipping is followed by root uprighting. Moreover, the bodily movement method in the edgewise technique most often requires the application of extraoral force supplied by headgear. Clinical experience indicates that the use of such extraoral force has caused hundreds of soft tissue injuries including many cases of partial and even total blindness as a result of accidents occurring while wearing headgear.

SUMMARY OF THE INVENTION

The present invention is in a combination edgewise bracket that can be used for obtaining tipping, uprighting and torquing movements, and for stabilizing a tooth in desired tip angulation. It includes a pair of horizontal slots adjacent to each other, one for coacting with an archwire to permit tipping and uprighting movements, and generally referred to as the tipping slot, and the other for coacting with a rectangular archwire to prevent tipping or uprighting movements or to obtain uprighting and/or torquing movements, and generally referred to as the horizontal uprighting slot. The bracket can also provide desired in and out movements. The slots are in communicating alignment with each other, whereby a wire in the position of the torquing slot can move between the slots.

A feature of the invention is to provide means that block out the archwire slot which concerns torquing movement when using the bracket for tipping or uprighting movement. The slot for torquing can also be used to stabilize the tooth in the desired uprighted position automatically where the archwire would move from the tipping slot into the torquing slot once the torquing slot aligns with the archwire.

While the combination edgewise bracket of the invention is particularly useful for moving teeth and closing spaces in a straight-wire technique, it can be used with any type of technique.

When using the bracket for crown tipping and root uprighting movements, it would coact with an archwire and have intraoral forces applied by use of suitable elastics, springs or other auxiliaries. When used for torquing movements, it may be subjected to intraoral forces or just the force applied by a rectangular archwire. Uprighting may also be obtained with a rectangular archwire in engagement with the rectangular uprighting slot.

For the purpose of accommodating the use of uprighting springs and other anchorable auxiliaries, a vertical slot may be provided in the base of the bracket at the tooth-mounting side. Long axis rotation control extensions, extending mesially and distally from the archwires slot allowing tipping and uprighting, may also be provided.

It is therefore an object of the present invention to provide a new and improved combination edgewise bracket for coacting with an archwire and suitable force-producing devices to move teeth through tipping, uprighting and torquing functions.

Another object of the present invention is in providing a combination edgewise bracket for use in edgewise and other techniques having first and second archwire slots, one of which may coact with an archwire in allowing tipping and uprighting with a spring and the other of which may coact with an archwire for producing torquing and uprighting functions.

A further object of the present invention is in the provision of a combination edgewise bracket for use in moving teeth which can substantially eliminate the need to apply extraoral forces.

A further object of the present invention is to provide a combination edgewise bracket for use in repositioning teeth anterior/posteriorly which can substantially eliminate the use of headgear.

Another object of the invention is in the provision of a combination bracket having two aligned slots for effecting uprighting and automatically stabilizing the tooth in the desired uprighted position.

Other objects, features and advantages of the invention will be apparent from the following detailed disclosure, taken in conjunction with the accompanying sheets of drawings, wherein like reference numerals refer to like parts, in which:

BRIEF DESCRIPTION OF THE DRAWINGS

FIG. 1 is a perspective view of one form of the present invention illustrated with archwires in position in both archwire slots;

FIG. 2 is a view like that of FIG. 1 with a slot blocking ligature in one of the archwire slots and illustrating an archwire in operation in the other slot;

FIG. 3 is a perspective view of a modified bracket according to the invention with a modified structure for permitting the use of a blocking ligature to block use of the interior rectangular uprighting slot and also illustrating the use of an uprighting spring;

FIG. 4 is a perspective view of a further modified bracket according to the invention wherein the rectangular uprighting slot is positioned exteriorly of the tipping slot and showing the use of an archwire in the tipping slot;

FIG. 5 is a side elevational view of the bracket of FIG. 4 and illustrating the manner in which a round wire is disposed in the tipping slot and a rectangular wire is disposed in the uprighting slot;

FIG. 6 is a side elevational view of the embodiment of FIG. 4 and illustrating the use of a rectangular wire filling both the tipping and edgewise slots; and FIG. 7 is a perspective view of a further modified bracket having twin tie wings and the rectangular uprighting slot exterior of said tipping slot.

DESCRIPTION OF THE INVENTION

The bracket of the invention may be generally referred to as a combination edgewise bracket since it includes a ligature tie wing and a pair of horizontally opening archwire slots. One of the slots would generally receive a round archwire to permit tipping and uprighting with a spring and will be generally referred to as the tipping slot, while the other slot would receive a rectangular wire to obtain torquing and/or uprighting and will generally be referred to as a rectangular uprighting slot.

The bracket may function in the movement of teeth mesiodistally through a combination of tipping and uprighting actions and to also maintain a desired upright position. It also can function to coact with a rectangular archwire to produce torquing and/or uprighting movements. Both round and rectangular archwires may be used depending upon the function desired.

While the bracket may be used in any one of the edgewise techniques, it may also be used in other techniques. Normally it will be used in a system having edgewise type brackets and in the straight-wire technique which is one form of an edgewise technique.

Teeth that require orthodontic treatment are quite often tipped mesiodistally at the beginning of or during the course of treatment. The tipping archwire slots in the brackets of the invention permit the initial engagement of an archwire in brackets on such tipped teeth with little or no deflection. Deflecting the archwire could require a greater force to be applied and/or result in loss of control in the vertical dimension, i.e., the undesired depression and/or elongation of teeth. One of the archwire slots in the bracket of the invention permits the teeth to tip mesiodistally during treatment without deflecting the archwire.

With respect to the bracket of the invention when used during the tooth-moving process, elastic traction devices and/or springs may be used to apply forces of a magnitude that could overpower a highly resilient archwire such as of the nickel titanium or metal core plastic type. It is therefore advantageous to use a relatively stiff or rigid archwire during this process. The archwire may be disposed in substantially parallel relation to the occlusal plane even when engaged in mesiodistally tipped teeth. Thus, the archwire can be of a size and stiffness compatible with the reciprocal movement forces to be encountered so that the tipping and uprighting movements produced will give the desired results.

The bracket of the invention can be made of a suitable metal, such as stainless steel, and it may be machined, sintered or cast in any known manner. The bracket may be made and then suitably secured to a base that would be bondable to a tooth, or the bracket and base may be cast together as a single unit. While it is preferred that the bracket be made of metal, it will be appreciated that it could be made of ceramic or plastic or plastic with a metal lined archwire slot. It is important that the bracket have sufficient strength to withstand the forces employed during the tooth-moving process. It may also be appreciated that the bracket may otherwise be attached to a tooth by the usual banding methods. In all cases the bracket will be mounted to the crown of the tooth and aligned with the long axis of the crown so that the tooth will attain the position finally desired.

For purposes of describing the invention and in order to promote clarity, the drawing illustrations relate principally to the use of the bracket in the straight-wire technique wherein the main archwire will be disposed in substantially parallel relation to the occlusal plane and where the rectangular slot of each bracket may be different to achieve or maintain varying degrees of root uprighting and torquing according to the desires of the orthodontist and the needs of each patient.

Referring now to the drawings and particularly to the embodiment of FIGS. 1 and 2, one bracket embodiment of the invention is illustrated and generally designated by the numeral 10. The bracket 10 includes generally a base portion 11 and a single tie wing 12 extending therefrom. The tie wing 12 includes upper and lower tie wing tips 13 and 14 which define a buccolabial opening horizontal archwire slot 15 that may receive an archwire and permit free tipping and uprighting movements, and generally referred to as the tipping slot. A round archwire 16 is illustrated as being received by the archwire slot 15. The base portion includes a buccolabially opening horizontal archwire slot 19 of rectangular cross section throughout its length for receiving an archwire and coacting therewith to stabilize the bracket against tipping or uprighting movements, and when using a rectangular wire to provide torque and/or uprighting movements. Slot 19 is generally referred to as the horizontal uprighting slot.

The base portion is rectangularly shaped and provided with opposed parallel and vertically arranged side walls 23 and 24, upper and lower walls 25 and 26 extending parallel to each other and also at right angles to the side walls. The parallel relationship is not critical to the invention, but may assist the orientation on a tooth during mounting procedures. An outer buccolabial face 27 has the tie wing integrally formed therewith. The back side 28 of the base portion is suitably attached to a base or pad 29. It will be appreciated that the base or pad 29 is of a type that can be directly bonded to the clinical crown of a tooth in the desired position. Further, it will be appreciated that the bracket may be suitably mounted onto a band which in turn could be cemented to a tooth.

The bracket is preferably mounted centrally on the base or pad and so that the side walls and upper and lower walls parallel the respective edges of the base or pad. As already mentioned, the bracket and pad would be mounted on the clinical crown of a tooth so that the vertical axis of the bracket substantially aligns with the long axis of the clinical crown.

The tipping and uprighting slot 15 is defined by a pair of opposed parallel pivotal edges 33 and 34 which extend labiolingually and provide pivot points relative to the archwire 16. The pivot edges define a rectangular cross section which may have any desired torquing angle. This slot is "Sved shaped." Diverging from the pivot edges 33 and 34 are inclined surfaces 37, 38, 39 and 40. The inclinations of the surfaces 37 to 40 exceed any desired tipping or uprighting angle normally encountered relative to the archwire. The inclinations of these surfaces are substantially equal as to value when measured from the horizontal.

The mesial and distal side walls of the tie wing 12 are parallel to each other and are defined as 47, 48, 49 and 50. It may be appreciated that side walls 47 and 48 are coplanar, while side walls 49 and 50 are coplanar. Additionally, these side walls are parallel to the side walls 23 and 24 of the base portion of the bracket as well as the side edges of the base or pad 29. Again, this parallel relationship is optional and not critical.

As above stated, the rectangular uprighting archwire slot 19 is in the face of the base porton 11, and it also aligns with the tipping slot 15. It will have an angle of inclination relative to the horizontal to correspond to the tip angle desired of the tooth it is designed for so that once the proper tip angle is achieved, the bracket and tooth can be maintained at that desired angle. It will also have a desired torque which would be the same as that in the tipping slot. Commonly used ideal or desired angles of inclination or torque for each particular tooth have long been proposed, but those angles may be varied in accordance with the discretion of the orthodontist in treating a particular pateint.

The angle of inclination is measured to the distal between the vertical axis of the mouth and the long axis of the clinical crown of a tooth. For example, the common ideal angles of inclination for the upper teeth, left and right, are:

5 degrees for a central,
9 degrees for a lateral,
11 degrees for a cuspid,
2 degrees for a bicuspid, and
5 degrees for a molar.

The common inclination angles for lower teeth, left and right, are:
2 degrees for centrals and laterals,
5 degrees for the cuspids, and
2 degrees for the bicuspids and molars.

While not illustrated, it will be appreciated that any archwire may be suitably ligated to the bracket 10 by a wire or elastic ligature, as seen in FIGS. 2 and 4 to 6. In order to show the fit of a rectangular archwire as seen in FIG. 1, a rectangular archwire 54 is received in the rectangular uprighting archwire slot 19. In some applications for certain treatment goals, both round and rectangular archwires will be used at the same time, as shown in FIG. 1. In such use the inner wire 54 may be highly flexible for mesiodistal uprighting and/or torque functions, while the outer wire 16 may be stiff or rigid for obtaining vertical and horizontal stability while yet permitting tip and torque movements.

When using the bracket 10 for tipping movements, it is preferable to block the rectangular uprighting slot 19 so that the main archwire 16 will not be able to move into slot 19. One easy method of blocking the slot is to use a blocking elastic ligature 58 as shown in FIG. 2 so that the archwire 16 will always be disposed in the tipping and uprighting slot 15 during relative movement between the bracket and the archwire. The rectangular uprighting slot may also be blocked by other methods such as tack welding a length of wire in the slot or a cap over the slot. Thus, an extra precaution is taken so as not to interfere with the plan of treatment.

The blocking elastic ligature 58 is as shown threaded into the slot 19 and then over the upper tie wing tip 13. Once the tipping function has been completed, the ligature may be removed during the uprighting function so that the slot 19 will be open and will be in full communication with the tipping slot 15. Then, once the desired tip angle is reached during uprighting of the root, the archwire 16 will automatically slip into or move into the slot 19 so that the desired uprighted position is stabilized and retained and overuprighting is prevented. It will here be appreciated that the angle of inclination and torque of the slot 19 will be such as to provide the desired tip angle or inclination angle and torque angle as above referred to.

Another form of structure that will permit the use of a blocking ligature and serve to block the torquing slot 19 is shown in the bracket 10A in FIG. 3 wherein vertically extending slots or recesses 61 and 62 are formed in the face of the rotation extensions on the base portion 11 mesial and distal of the tie wing 12 for receiving a blocking ligature. While no blocking ligature is shown in FIG. 3, it will be appreciated that the ligature will be threaded in the recesses 61 and 62 and over both the upper and lower tie wing tips 13 and 14 whereby the ligature will cross the archwire slot 19 both mesially and distally of the tie wing and effectively serve to block entry of the archwire 16 into the slot 19. As already described in connection with the blocking feature in bracket 10, as shown in FIG. 2, once the tipping movement has been completed, the blocking ligature may be removed so that during root uprighting the archwire 16 may fall into the slot 19 when the desired uprighting position has been attained.

Also illustrated in FIG. 3 is the use of an uprighting spring 65 having a tail 66 received in a vertical slot 67 formed in the base portion 11 along the vertical central axis of the bracket in the usual manner for producing root uprighting. This uprighting spring 65 includes a lever arm 68 and coils 69 where the lever arm is hooked over the archwire. This spring may be used as a tipping spring when the lever arm is applied to the archwire at the other side of the bracket to cause a tipping movement. Further, the spring 65 will provide the intraoral force necessary for tipping or uprighting movement, while in FIG. 1 the highly resilient rectangular wire 54 could be used to provide that movement.

Except for the manner in which a blocking ligature is received in the slots 61 and 62 of bracket 10A, the operation of that bracket is identical to the bracket of FIGS. 1 and 2. It may also be appreciated that the tipping slot 15 is disposed labially or buccally of the torquing slot 19. It may be further appreciated that while a round wire is shown as the main archwire for the tipping slot, a rectangular archwire could be disposed in the tipping slot and the tipping and uprighting functions obtained as above explained. Further, it may be appreciated that once the attempted inclination angle is reached and the round wire is received in the inner rectangular slot 19, it may be exchanged for a rectangular wire so that torquing movements can be obtained for more precision positioning of the tooth.

Although the labiolingual dimension of the rectangular wire 54 is illustrated as substantially equaling the depth of the rectangular archwire slot 19, it may equal to entire labiolingual depth of both slots 15 and 19 particularly where it is desired to provide a stiffer archwire for control purposes and where treatment has progressed where no further uprighting movement is desired.

Another embodiment of the invention is illustrated in FIGS. 4 to 6 in the bracket 10B which differs principally from the brackets 10 and 10A in that the tipping slot is disposed lingually of the horizontal uprighting slot. The bracket 10B includes a base portion 70 and extending therefrom a tie wing 71. The base portion is in the form of a flat plate 72 of greater mesiodistal dimension that the mesiodistal dimension of the tie wing, together with upper and lower triangularly shaped blocks 73 and 74 which coact to define therebetween the tipping slot 75 of the bracket in the same fashion as the tipping slot 15 is defined by the tips of the tie wing brackets 10 and 10A. The opposed mesial and distal walls or sides of the flat plate 72 are parallel to each other and also parallel to the opposed side edges of the base or pad 29, and the upper and lower side walls of the flat plate are likewise parallel to each other and parallel to the upper and lower edges of the pad 29 in the same manner as the base portion of the brackets 10 and 10A. The edges of the base portion and the pad assist in properly mounting the bracket and pad onto a tooth in the desired alignment particularly with the long axis of the clinical crown. As above, the parallel arrangements are not critical.

The tie wing 71 is disposed outward of the tipping and uprighting slot blocks 73 and 74 and includes upper and lower tie wing tips 77 and 78 defining a rectangular archwire slot 82. Similarly, tne mesial and distal sides of the tie wing and the occlusal and gingival edges are parallel to each other and at right angles and parallel to the outer respective edges of the base portion and the pad. The parallel relation can assist in orienting the bracket on a tooth, but it is not critical to the invention. The slot 82 aligns with the tipping slot 75 but is disposed labially or buccally to the slot 75. Additionally, the tie wing tips more than cover the blocks 73 and 74 so that more positive rotational control is obtained when the archwire 16 is angulated relative to the bracket and therefore disposed between the tie wings and the base plate.

In operation, the bracket 10B will permit the same tipping and uprighting functions as previously described when the archwire is aligned with the tipping slot 75, as shown in FIG. 4. A suitable ligature can be provided to hold the archwire in this slot. Once the appropriate tipping or uprighting function associated with the tipping slot has been completed, it is then necessary to add the rectangular archwire such as archwire 54 in FIG. 5, which fills the uprighting slot 82, thereby to further upright or provide stability against further movement.

Alternatively, the round wire may be removed and a stiffer rectangular wire having a labiolingual depth equal to the depth of both archwire slots may be used, as illustrated by the archwire 85 in FIG. 6, and where the archwire would fully cover the entire depth of both archwire slots. An elastic wire retaining ligature 88 is illustrated in place in FIG. 4 over just the round wire 16, in FIG. 5 over the round wire 16 and the rectangular wire 54, and in FIG. 6 over the rectangular archwire 85. It may be appreciated that other types of ligatures may be provided for retaining the archwire in place on the bracket.

A modification of bracket 10B is shown in FIG. 7 and generally designated as 10C, which differs only in that it includes a pair of tie wings 90 and 91, both of which embrace the rectangular uprighting slot. Greater mesiodistal width is obtained in this embodiment for the usual purposes. This bracket will otherwise function in the same manner as bracket 10B.

While not illustrated, it should be appreciated that the present invention could also be incorporated in a bracket having a single tie wing tip on one side and double tie wing tips on the other side. For example, a bracket having a single incisal tie wing tip and double occlusal tie wings tips with the present double slot arrangement would come within the scope of the present invention.

The tip and torque will be designed into the bracket of the present invention according to the desired end result for any orthodontic treatment. Thus, tip and torque would be designed into the rectangular slot.

It will be understood that modifications and variations may be effected without departing from the scope of the novel concepts of the present invention, but it is understood that this application is to be limited only by the scope of the appended claims.

The invention is hereby claimed as follows:

1. A combination edgewise bracket comprising, a base portion and a tie wing extending buccolabially from the base portion, first and second horizontally opening and horizontally aligned archwire slots formed in said base portion and said tie wing, one of said slots being Sved shaped to coact with an archwire and allow free tipping, and the other of said slots being rectangular to coact with an archwire and obtain uprighting and torquing, and said second slot opening into said first slot, whereby said Sved slot will permit tipping and uprighting movements when aligned with an archwire, and said rectangular slot will prevent tipping or uprighting movements when aligned with an archwire and will provide torquing movement when aligned with a mating rectangular archwire.

2. The combination defined in claim 1, wherein said Sved shaped slot is in said tie wing and said other slot is in said base portion.

3. The combination defined in claim 2, wherein said bracket further includes means for blocking said other slot.

4. The combination defined in claim 2, wherein said bracket further includes means coactable with an endless elastic member to block the slot in the base portion from receiving an archwire.

5. The combination defined in claim 1, wherein said Sved shaped slot is in the base portion and said other slot is in the tie wing.

6. The combination defined in claim 1, wherein said rectangular slot when coacting with a rectangular wire controls torquing and/or uprighting movements.

7. The combination defined in claim 1, wherein said rectangular slot is lingual to the Sved slot.

8. The combination defined in claim 1, wherein said rectangular slot is labial to the Sved slot.

9. The combination defined in claim 8, wherein said bracket includes a single tie wing.

10. The combination as defined in claim 8, wherein said bracket includes a pair of tie wings.

11. A combination edgewise bracket for selective use in crown tipping, root uprighting or torquing, said bracket comprising a body portion and at least one tie wing extending from the body with at least one upper and at least one lower tie wing tip, a mesiodistally extending labiobuccally opening crown tipping slot between said tips defined by opposed labiolingual edges and surfaces diverging from the edges such that the inclination of said surfaces is greater than the range of tipping or uprighting desired, and a labiobuccally opening rectangular uprighting archwire slot in said body portion for coacting with an archwire to prevent tipping or to effect torquing and uprighting, said uprighting slot being labiolingually aligned with said tipping slot such that an archwire in one slot can move to the other slot along a labiolingual axis, whereby said crown tipping slot will permit tipping and uprighting movements when aligned with an archwire, and said rectangular slot will prevent tipping or uprighting movements when aligned with an archwire and will provide torquing movement when aligned with a mating rectangular archwire.

12. The combination of claim 11, wherein torque control is produced when a rectangular wire coacts with said rectangular uprighting slot or said tipping slot.

13. The combination of claim 11, which further includes recess means in said base portion for coacting with said tie wing tips for receiving an elastic blocking ligature to block entry into said base portion slot.

14. The combination of claim 11, which further includes an elastic blocking ligature filling the base portion slot to block the entry of an archwire.

15. A combination edgewise bracket comprising, a body portion and a tie wing extending therefrom having upper and lower tie wing tips, a first mesiodistally extending archwire slot between said wing tips, a second mesiodistally extending archwire slot in said body portion, said slots being aligned such that an archwire in one slot may move directly into the other slot, one of said slots having pivot edges to coact with a round or rectangular archwire for allowing tipping and uprighting movements, and the other of said slots being rectangular in cross section throughout its length to coact with a mating rectangular archwire for preventing tipping or effecting uprighting movements while permitting torquing movements, whereby said one slot will permit tipping and uprighting movements when aligned with an archwire, and said other slot will prevent tipping or uprighting movements when aligned with an archwire and will provide torquing movement when aligned with a mating rectangular archwire.

16. A combination edgewise bracket for selective use in crown tipping, root uprighting or torquing, said bracket comprising a body portion and a tie wing extending from the body with upper and lower tie wing tips, a mesiodistally extending labiobuccally opening tipping archwire slot between said tips defined by opposed labiolingual edges and surfaces diverging from the edges such that the inclination of said surfaces is greater than the range of tipping or uprighting desired, a labiobuccally opening mesiodistally extending rectangular uprighting archwire slot in said body portion and in alignment with said tipping and uprighting archwire slot such that an archwire in one slot may move directly into the other slot or an archwire of sufficient depth may extend through the depth of both slots, said rectangular uprighting slot being angularly disposed such that when aligned with the main archwire the tooth will be at the desired tip angle, and a removable elastic blocking ligature filling said rectangular slot during tipping and removable during uprighting, whereby an archwire in the tipping slot automatically moves into the rectangular slot in the absence of a blocking ligature when the tooth is uprighted to the desired tip angle to prevent further uprighting movement, and further said tipping slot will permit tipping and uprighting movements when aligned with an archwire, and said rectangular slot will prevent tipping or uprighting movements when aligned with an archwire and will provide torquing movement when aligned with a mating rectangular archwire.

17. The combination of claim 16, which further includes means for blocking the rectangular uprighting slot during tipping movement.

* * * * *